US00PP37841P3

(12) United States Plant Patent
Jones

(10) Patent No.: US PP37,841 P3
(45) Date of Patent: Nov. 10, 2026

(54) ***IPOMOEA* PLANT NAMED 'ISGBE15-1'**

(50) Latin Name: *Ipomoea batatas*
Varietal Denomination: ISGBE15-1

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 19/550,007

(22) Filed: Feb. 25, 2026

(65) Prior Publication Data

US 2026/0271813 P1 Sep. 10, 2026

Related U.S. Application Data

(60) Provisional application No. 63/768,968, filed on Mar. 8, 2025.

(51) Int. Cl.
*A01H 5/00* (2018.01)
*A01H 5/12* (2018.01)
*A01H 6/00* (2018.01)

(52) U.S. Cl.
USPC ..... Plt./258
CPC ..... *A01H 6/00* (2018.05); *A01H 5/12* (2013.01)

(58) Field of Classification Search
USPC ..... Plt./226, 258
See application file for complete search history.

(56) References Cited

U.S. PATENT DOCUMENTS

PP25,260 P2 * 1/2015 Schaber ..... A01H 6/42 Plt./332
PP32,057 P2 * 8/2020 Jones ..... A01H 6/00 Plt./258

OTHER PUBLICATIONS

GreenFuse botanicals, inc. website. 2016. https://green-fuse.com/new/ipomoea-sweet-georgia/ (Year: 2016).*
Garden Center Marketing. https://www.gardencentermarketing.com/plantName/Ipomoea-batatas-sweet-georgia-Pulse-black?srsltid=AfmBOopY-T46TyXWSVdeQ-PXydL-ZvhchyRPI4R3R9fe6Lx-D3tbBYi9. (Year: 2025).*

* cited by examiner

*Primary Examiner* — Karen M Redden

(57) ABSTRACT

A new and distinct cultivar of *Ipomoea* plant named 'ISGBE15-1' is disclosed, characterized by dark greyed-purple shiny foliage with a jagged margin. Plants have short internodes. The new cultivar is a *Ipomoea* typically produced as an outdoor ornamental plant.

2 Drawing Sheets

Latin name of the genus and species: *Ipomoea batatas.*
Variety denomination: 'ISGBE15-1'.

BACKGROUND OF THE INVENTION

The new variety originated as a chance discovery by the inventor. The variety was discovered as a naturally occurring whole plant mutation from an unnamed, unpatented proprietary variety of *Ipomoea batatas*. The new variety was discovered in March 2023 at a commercial greenhouse in Somis, California.

After selecting and isolating the new cultivar, asexual reproduction of the new cultivar 'ISGBE15-1' was first performed by vegetative tip cuttings in a commercial greenhouse in Somis, California in August 2023. 'ISGBE15-1' has since produced several generations and has shown that the unique features of this cultivar are stable and reproduced true to type. Typical asexual reproduction of the new variety is by vegetative cuttings.

SUMMARY OF THE INVENTION

The cultivar 'ISGBE15-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ISGBE15-1'. These characteristics in combination distinguish 'ISGBE15-1' as a new and distinct *Ipomoea* cultivar:

1. Dark greyed-purple leaves.
2. Edge of leaf is jagged, creating a sawtooth appearance.
3. Short internodes.
4. Glossy upper foliage surface.

PARENTAL COMPARISON

Plants of the new cultivar 'ISGBE15-1' are similar to the parent in most horticultural characteristics. However, 'ISGBE15-1' differs in the following:

1. Leaves of the new variety are larger and wider than leaves of the parent.
2. Leaves of the new variety have a more sawtooth edge than leaves of the parent.
3. Plants of the new variety are larger than plants of the parent.

COMMERCIAL COMPARISONS

Plants of the new cultivar 'ISGBE15-1' can be compared to the unpatented commercial variety *Ipomoea batatas*, 'ISGHP05-2' U.S. Plant Pat. No. 31,726. Plants of 'ISGBE15-1' are similar to plants of, 'ISGHP05-2' in some horticultural characteristics, however, plants of 'ISGBE15-1' differ in the following:

1. Leaves of the new variety are glossier than leaves of this comparator.
2. Leaves of the new variety are broader and larger than leaves of this comparator.
3. Leaves of the new variety have a more sawtooth edge than leaves of this comparator.
4. Internodes of the new variety are shorter than internodes of this comparator.

BRIEF DESCRIPTION OF THE PHOTOGRAPHS

Figure 1:
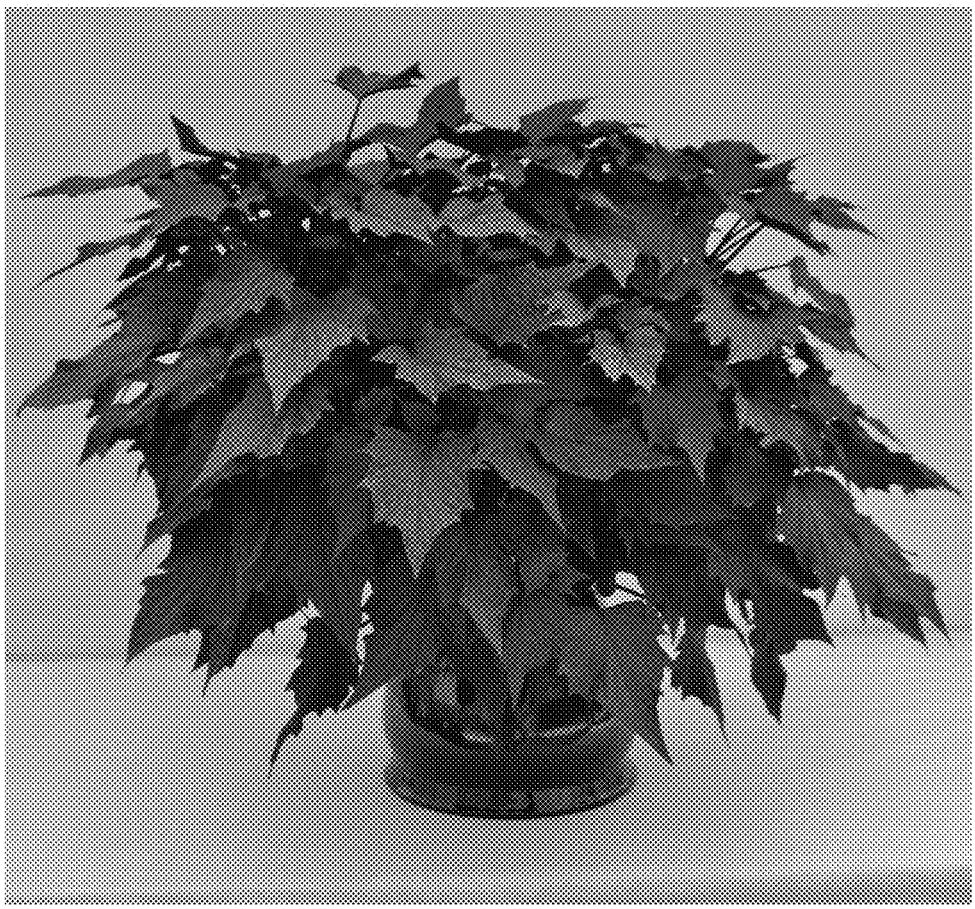

The accompanying photograph in FIG. 1 illustrates in full color a typical plant of 'ISGBE15-1' grown in a greenhouse in Somis, California. This plant is approximately 1-year old, shown in a 12-inch pot.

Figure 2:
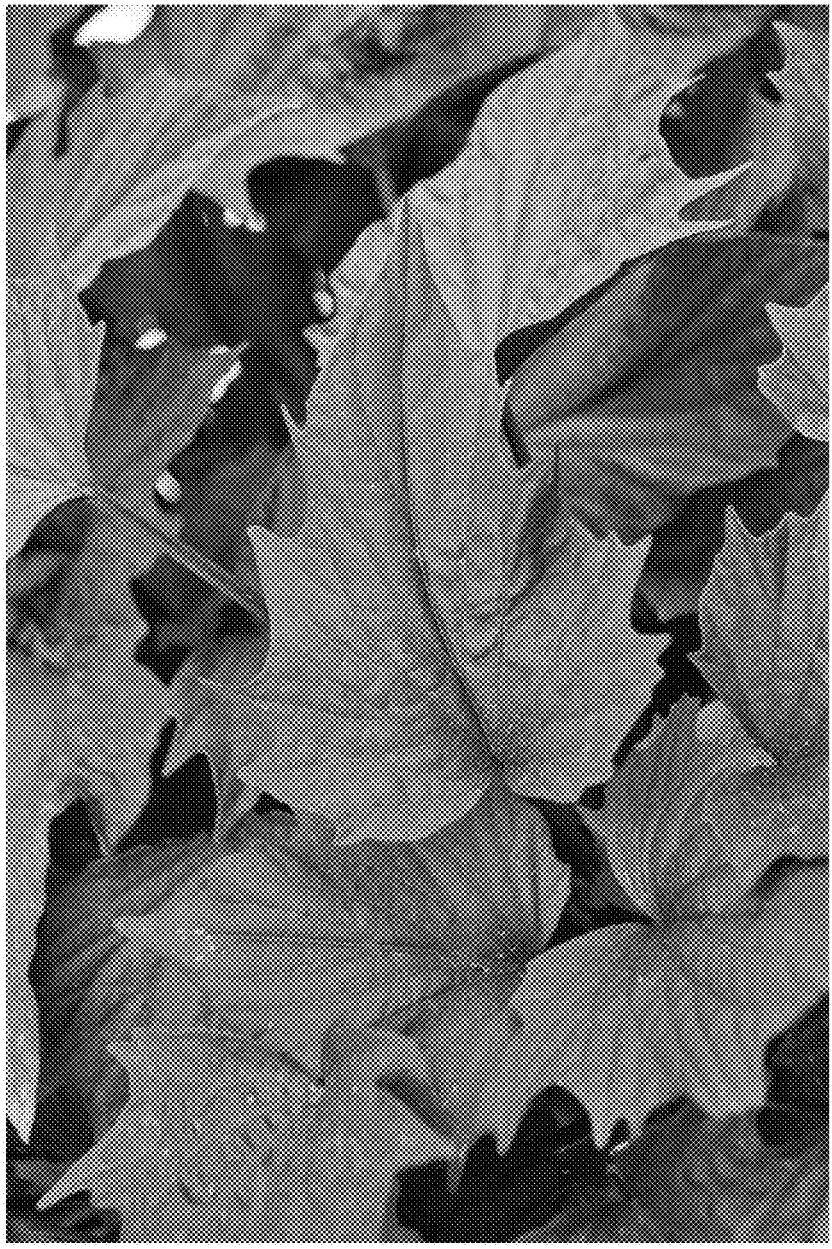

FIG. 2 illustrates a close-up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The R.H.S. Colour Chart, 2007, except where general terms of ordinary dictionary significance are used. The following observations and measurements describe 'ISGBE15-1' plants grown during the Spring months in a greenhouse in Somis, California, under bright, unshaded conditions. Average day temperatures were approximately 20° C. to 26° C. and the average night temperature was approximately 15° C. to 18° C. No artificial light, photoperiodic treatments or chemical treatments were given to the plants. Measurements and numerical values represent averages of typical plant types.

Botanical classification: *Ipomoea batatas* 'ISGBE15-1' Pulse Black.

Age of the plant described: Approximately 8 weeks from an unrooted cutting.

Container size of the plant described: 6 inches.

PROPAGATION

Propagation method: Terminal cuttings.

Time to develop roots suitable for transplanting:

*Summer*.—About 6 days at an average temperature of 24° C.

*Winter*.—About 10 days at an average temperature of 24° C.

Root description: Thick, fleshy. Roots colored closest to RHS Yellow-White 158A.

Tuber description: Not observed to date.

*Growth habit*.—Semi-compact, and mounding. Dense and bushy.

*Height*.—Measured from top of soil line of pot, approximately 25 cm.

*Plant spread*.—Approximately 35 cm.

*Growth rate*.—Rapid.

*Branching characteristics*.—Very free branching, alternate or whorled occurring.

Primary lateral branches:

*Length*.—7 to 14 cm.

*Diameter*.—Approximately 0.7 cm.

*Texture*.—Glabrous.

*Color*.—Near RHS Greyed-Purple 187B.

*Strength*.—Strong.

*Internode length*.—3 to 8 mm.

*Adventitious roots at nodes*.—Not observed.

Secondary lateral branches:

*Length*.—4 to 8 cm.

*Diameter*.—Approximately 0.4 cm

*Texture*.—Glabrous.

*Color*.—Near RHS Greyed-Purple 187B.

*Strength*.—Flexible.

*Internode length*.—3 to 6 mm.

*Quantity per 8 week old plant*.—Approximately 15.

*Adventitious roots at nodes*.—Not observed.

New shoot growth characteristics:

*Color*.—Near RHS Greyed-Purple 187C.

*Aspect*.—Upright.

*Texture*.—Glabrous.

FOLIAGE

Leaf:

*Arrangement*.—Whorled and alternate, simple.

*Average length*.—6 to 9 cm.

*Average width*.—5 to 7 cm.

*Shape of blade*.—Cordate with 4 to 6 shallow sinuses.

*Apex*.—Acute.

*Base*.—Shallow cordate.

*Margin*.—Entire.

*Aspect*.—Upward fold and petiole attachment. Young foliage more folded.

*Texture of top surface*.—Glabrous.

*Texture of bottom surface*.—Glabrous.

*Appearance of top surface*.—Glossy.

*Appearance of bottom surface*.—Matte.

*Quantity of leaves per lateral branch*.—Average 6 to 12.

Foliage color:

*Young foliage upper side*.—Near RHS Greyed-Purple187A flushed N186D. Veins 187D. Interior young foliage Yellow-Green 145B flushed 187B along margins.

*Young foliage under side*.—Near RHS Greyed-Purple N186C, strongly flushed N186D. Veins N186D. Interior young foliage Yellow-Green 144C flushed 187C along margins.

Venation:

*Type*.—Palmate, reticulate.

Petiole:

*Length*.—Approximately 2 to 3.5 cm.

*Diameter*.—Approximately 4 mm at base, 3 mm at leaf attachment.

*Texture*.—Glabrous.

*Color*.—Near RHS Greyed-Purple N186C.

*Strength*.—Strong.

*Aspect*.—Straight to slightly curved.

FLOWER

Flowering not observed to date.

OTHER CHARACTERISTICS

Seeds and fruits: No seeds/fruits observed.

What is claimed is:

1. A new and distinct cultivar of *Ipomoea* plant named 'ISGBE15-1' as herein illustrated and described.

* * * * *